US006540893B1

(12) United States Patent
Wakida et al.

(10) Patent No.: US 6,540,893 B1
(45) Date of Patent: Apr. 1, 2003

(54) ION SENSOR (75) Inventors: Shinichi Wakida, Ikeda (JP); Yoshiro Tatsu, Ikeda (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/642,106

(22) Filed: Aug. 21, 2000

(30) Foreign Application Priority Data

Aug. 23, 1999 (JP) .......................................... 11-234920

(51) Int. Cl.$^7$ ............................................. G01N 27/333
(52) U.S. Cl. ...................... 204/416; 204/418; 204/419
(58) Field of Search ............................... 204/403, 416, 204/418, 419, 415, 403.01

(56) References Cited

U.S. PATENT DOCUMENTS 4,894,339 A * 1/1990 Hanazato et al. ............ 435/182
5,204,239 A    4/1993 Gitler et al.

FOREIGN PATENT DOCUMENTS

| JP | 6-90736    |   | 3/1986 |
|----|------------|---|--------|
| JP | 01170848 A | * | 7/1989 |
| JP | 61-60698   |   | 4/1994 |
| WO | WO-97-37215|   | 9/1997 |

OTHER PUBLICATIONS

Polypeptide entry in the online Encyclopedia of Molecular Biology (1999, John Wiley & Sons, Inc.) posted Jan. 15, 2002.*

English language translation of Suetsugu et al. (JP 01170848 A) Jul. 5, 1989.*

CAPLUS abstract of Maeda et al. ("Biomembrane–mimetic ion sensors based on multiphase material containing synthetic polypeptide as sensitizer", J. Chem. Soc., Chem. Commun. (19900, 921), 1529–31).*

CAPLUS abstract of Suetsugu et al. (JP 01170848 A).*

Derwent abstract of Suetsugu et al. (JP 01170848 A).*

* cited by examiner

Primary Examiner—T. Tung
Assistant Examiner—Alex Noguerola
(74) Attorney, Agent, or Firm—Rader, Fishman & Grauer PLLC (57) ABSTRACT

An object of the present invention is to provide an electrode and a field effect transistor having excellent ion selectivity using a noncyclic peptide. In order to achieve the above object, the ion sensor of the present invention using a noncyclic peptide is an ion sensor where a noncyclic peptide is contained in a sensing membrane. The said noncyclic peptide may contain at least two kinds of natural amino acids or non-natural amino acids. The ion sensor of the present invention may be constituted by an ion-selective electrode or by an ion-selective field effect transistor. Examples of the main responding ion are magnesium ion, lead ion, potassium ion, calcium ion, nickel ion, copper ion, zinc ion and cadmium ion.

16 Claims, 12 Drawing Sheets

An example of the constitution of an ion-selective electrode

Fig. 1

An example of the constitution of an ion-selective electrode

Interfering ions $Ca^{2+}$, $Mg^{2+}$, $Ni^{2+}$, $Cd^{2+}$, $Zn^{2+}$, $Cu^{2+}$ ($10^{-1}$ M)

Fig. 14

ION SENSOR

BACKGROUND OF THE INVENTION

The present invention relates to an ion sensor using a noncyclic peptide.

Ion sensor such as an ion-selective electrode and an ion-selective field effect transistor is a quick and convenient sensor where measurement of ion in a solution can be carried out merely by dipping it in a solution to be measured. For example, an electrode using valinomycin which is a cyclic peptide exhibits a selectivity to potassium ion and has been widely used for measurement of the electrolytes in blood. Studies of cyclic peptides have been carried out by biomimetic function of the potassium ion channel, valinomycin but there has been no example of the study for ion-selective electrodes and ion-selective field effect transistors using noncyclic peptides.

SUMMARY OF THE INVENTION

An object of the present invention is to provide an electrode and a field effect transistor having excellent ion selectivity using a noncyclic peptide.

In order to achieve the above object, the ion sensor of the present invention using a noncyclic peptide is an ion sensor where a noncyclic peptide is contained in an ion-sensing membrane.

The said noncyclic peptide may contain at least two kinds of natural amino acids or non-natural amino acids.

The ion sensor of the present invention may be constituted by an ion-selective electrode or by an ion-selective field effect transistor.

DETAILED DESCRIPTION OF THE PREFERRED EMBODIMENTS

Numbers of the amino acid in the noncyclic peptide used in the present invention are 4~20 and, preferably, 5~12.

Examples of the amino acid are alanine, proline, valine, leucine, serine, tryptophan, asparagine and histidine. Preferred noncyclic peptides are the noncyclic peptides containing proline as an essential component and also containing at least one amino acid selected from a group consisting of natural L- or D-amino acid except proline and non-natural amino acid such as amino acid made into a derivative as an optional component.

Type of the ion having a selectivity can be changed when the type and the length (amino acid numbers) of the noncyclic peptide are changed.

Particularly preferred examples are the noncyclic peptides having the following ten kinds of amino acid sequences. In the following formulae, A stands for alanine while P stands for proline.

PAAAPAAA; (PAAA)$_2$
APAAAPAA; (APAA)$_2$
AAPAAAPA; (AAPA)$_2$
AAAPAAAP; (AAAP)$_2$
APPAAPPA; (APPA)$_2$
PAPAPAPA; (PAPA)$_2$
PPAAPPAA; (PPAA)$_2$
APAPAPAP; (APAP)$_2$
PAAPPAAP; (PAAP)$_2$
AAPPAAPP; (AAPP)$_2$

An amino group at the N-terminal of the noncyclic peptide may form an amide bond with an alkanoyl group such as an acetyl group, a propionyl group or a dodecanoyl group or may be substituted with an alkyl group such as a methyl group, an ethyl group or a dodecanyl group, a benzyl group, a benzoyl group, etc.

The carboxyl group of the C-terminal of the noncyclic peptide may be COOH as it is or may be in a form of an acid amide (CONH$_2$) or an acid anilide.

The ion-selective electrode of the present invention is identical with the known ion-selective electrodes which are mentioned, for example, in U.S. Pat. No. 4,476,007 except that a noncyclic peptide is contained and it may be easily manufactured using a noncyclic peptide in place of conventionally used ion-sensing materials. The ion-selective electrode may be easily manufactured using, for example, an ion electrode kit (manufactured by Denki Kagaku Keiki).

An example of the ion-selective electrode according to the present invention is as follows.

Reference Electrode/Sample Solution/Ion-Selective Electrode Ag—AgCl/3M KCl/0.1M LiOAc/Sample Solution/Sensing Membrane/Inner Solution/Ag—AgCl The sample solution is a solution containing the ion to be measured and, usually, it is an aqueous solution. Examples of the ion to be measured are transition metal ion such as $Pb^{2+}$, $Ni^{2+}$, $Cu^{2+}$, $Zn^{2+}$ and $Cd^{2+}$; alkaline metal ion such as $K^+$, $Na^+$ and $Li^+$; alkaline earth metal ion such as $Ca^{2+}$ and $Mg^{2+}$; and $NH_4^+$.

Further, when a noncyclic peptide is used, the ion-selective field effect transistor of the present invention can be easily manufactured by a method known, for example, by U.S. Pat. No. 4,020,830. Thus, for example, a source of an n-type and a drain of an n-type are formed on a silicone base plate, they are coated with an $SiO_2$ insulating membrane and an $Si_3N_4$ passive membrane and then an ion-sensing membrane containing a noncyclic peptide is formed on the $Si_3N_4$ passive membrane whereupon an ion-selective field effect transistor is manufactured. Incidentally, as to an ion-sensing membrane for the ion-selective field effect transistor, a sensing membrane which is as same as for an ion-selective electrode may be used.

An example of the ion-selective field effect transistor according to the present invention is as follows.

[Reference Electrode/Sample Solution/Ion-Sensing Membrane/$Si_3N_4$, $SiO_2$/Channel]

The sensing membrane contains a noncyclic peptide (about 1–15% by weight of the whole membrane) and a membrane material (about 20–80% by weight of the whole membrane). To the same sensing membrane may be further added 0–15% by weight of an additive salt and 10–79% by weight of a plasticizer to the total weight of the membrane.

Examples of the membrane material are polyvinyl chloride (PVC), silicone resin, polyurethane urea, photo resist and Japanese lacquer.

Examples of the additive salt are sodium tetrakis[3,5-bis(trifluoromethyl)phenyl]borate (TFPB), potassium tetrakis(4-chlorophenyl)borate and sodium tetrakis[3,5-bis(1,1,1,3,3,3-hexafluoro-2-methoxy-2-propyl)phenyl]-borate.

Examples of the plasticizer are 2-nitrophenyl octyl ether (NPOE), 2-nitrophenyl dodecyl ether, 2-fluoro-2'-nitrodiphenyl ether, 2-nitrophenyl phenyl ether, dioctyl sebacate and dioctyl phthalate.

The sensing membrane can be manufactured in such a procedure that a noncyclic peptide and, if necessary, membrane material, additive salt, plasticizer, etc. are dissolved in a solvent such as tetrahydrofuran, the solution is made contained in a support such as a membrane filter made of Teflon (PTFE) and the solvent is evaporated.

There is no particular limitation for the inner solution and its examples are aqueous solution of metal salt such as aqueous solution of potassium chloride and aqueous solution of calcium nitrate; and a mixed solution of aqueous solution of potassium chloride with a aqueous solution of other metal salt.

With regard to a reference electrode, known electrodes may be used without limitation.

In accordance with the present invention, it is now possible to carry out a selective measurement of ion such as a lead ion.

EXAMPLES

The present invention will be further illustrated by way of the following Examples.

(1) Synthesis of noncyclic peptides

The following noncyclic peptides were synthesized with a solid-phase synthetic method.

Acetyl-Ala Pro Pro Ala Ala Pro Pro Ala-$NH_2$; hereinafter abbreviated as Ac(APPA)$_2$ Acetyl-Pro Ala Pro Ala Pro Ala Pro Ala-$NH_2$; hereinafter, abbreviated as Ac-(PAPA)$_2$ Acetyl-Pro Pro Ala Ala Pro Pro Ala Ala-$NH_2$; hereinafter, abbreviated as Ac-(PPAA)$_2$ Acetyl-Ala Pro Ala Pro Ala Pro Ala Pro-$NH_2$; hereinafter, abbreviated as Ac-(APAP)$_2$ Acetyl-Pro Ala Ala Pro Pro Ala Ala Pro-$NH_2$; hereinafter, abbreviated as Ac-(PAAP)$_2$ Acetyl-Ala Ala Pro Pro Ala Ala Pro Pro-$NH_2$; hereinafter, abbreviated as Ac-(AAPP)$_2$ (2) Preparation of standard solutions Calcium nitrate tetrahydrate was weighed in an amount of 11.808 g and made into a $10^{-1}$M aqueous solution of calcium nitrate using a 500-ml measuring flask. Then an operation of diluting the resulting aqueous solution to an extent of 10-fold was carried out repeatedly to prepare standard calcium nitrate solutions of $10^{-2}$M, $10^{-3}$M, $10^{-4}$M, $10^{-5}$M, $10^{-6}$M and $10^{-7}$M concentrations.

At the same time, 4.250 g of sodium nitrate, 5.055 g of potassium nitrate, 12.821 g of magnesium nitrate hexahydrate, 14.540 g of nickel nitrate hexahydrate, 15.424 g of cadmium nitrate tetrahydrate, 16.560 g of lead nitrate, 14.874 g of zinc nitrate hexahydrate and 12.080 g of copper nitrate trihydrate each were weighed and standard solutions of each of them having concentrations of $10^{-1}$M, $10^{-2}$M, $10^{-3}$M, $10^{-4}$M, $10^{-5}$M, $10^{-6}$M and $10^{-7}$M were prepared.

(3) Preparation of mixed solutions containing interfering ion

Nine kinds of interfering ions ($Na^+$, $K^+$, $Ca^{2+}$, $Mg^{2+}$, $Ni^{2+}$, $Cd^{2+}$, $Zn^{2+}$, $Cu^{2+}$ and $Li^+$) were selected and standard nitrate solutions each containing a predetermined amount of such an interfering ion were prepared and used for a mixed solution method.

Calcium nitrate tetrahydrate was weighed in an amount of 23.615 g and distilled water was added thereto using a measuring cylinder in a 1,000-ml measuring flask to prepare a $10^{-1}$M aqueous solution of calcium nitrate. Similarly were weighed 8.499 g of sodium nitrate, 10.110 g of potassium nitrate, 25.641 g of magnesium nitrate hexahydrate, 29.080 g of nickel nitrate hexahydrate, 30.847 g of cadmium nitrate tetrahydrate, 29.747 g of zinc nitrate hexahydrate, 24.160 g of copper nitrate trihydrate and 6.894 g of lithium nitrate to prepare $10^{-1}$M solutions respectively. Further, the aqueous solution of sodium nitrate was diluted to an extent of 10-fold to give a $10^{-2}$M aqueous solution.

Each of the above solutions was used instead of distilled water to prepare mixed solutions of lead nitrate (1M~$10^{-6}$M) where an interfering ion coexisted.

(4) Preparation of ion-selective electrodes

With a peptide regard to an ion-sensing material, 4% by weight of peptide [1] Ac-(APPA)$_2$, peptide [2] Ac-(PAPA)$_2$, peptide [3] Ac-(PPAA)$_2$, peptide [4] Ac-(APAP)$_2$, peptide [5] Ac-(PAAP)$_2$ or peptide [6] Ac-(AAPP)$_2$ was used; with regard to an additive salt, 1% by weight of sodium tetraphenylborate (TFPB) was used; and, with regard to a plasticizer, 65% by weight of 2-nitrophenyl octyl ether (NPOE) was used and they were dissolved in an optional amount of tetrahydrofuran (THF) with stirring. After the peptide was dissolved, 30% by weight of polyvinyl chloride (PVC) was added to the membrane materials and dissolved with stirring.

A membrane filter made of Teflon (PTFE) having a diameter of 6 mm was taken using a pincette and dipped in the above-prepared mixed solution in THF so that the solution was well permeated thereinto and placed on a groove of the chip at the end of an ion-selective electrode kit (manufactured by Denki Kagaku Keiki) in such a manner that the filter did not come up. THF was evaporated therefrom and, again, the mixed solution in THF was casted onto the membrane filter. Such an operation was repeated and, when the groove disappeared, the formation of a PVC membrane was judged to be completed. Outline of the ion-selective electrode kit will be explained by referring to FIG. 1.

Figure 1:
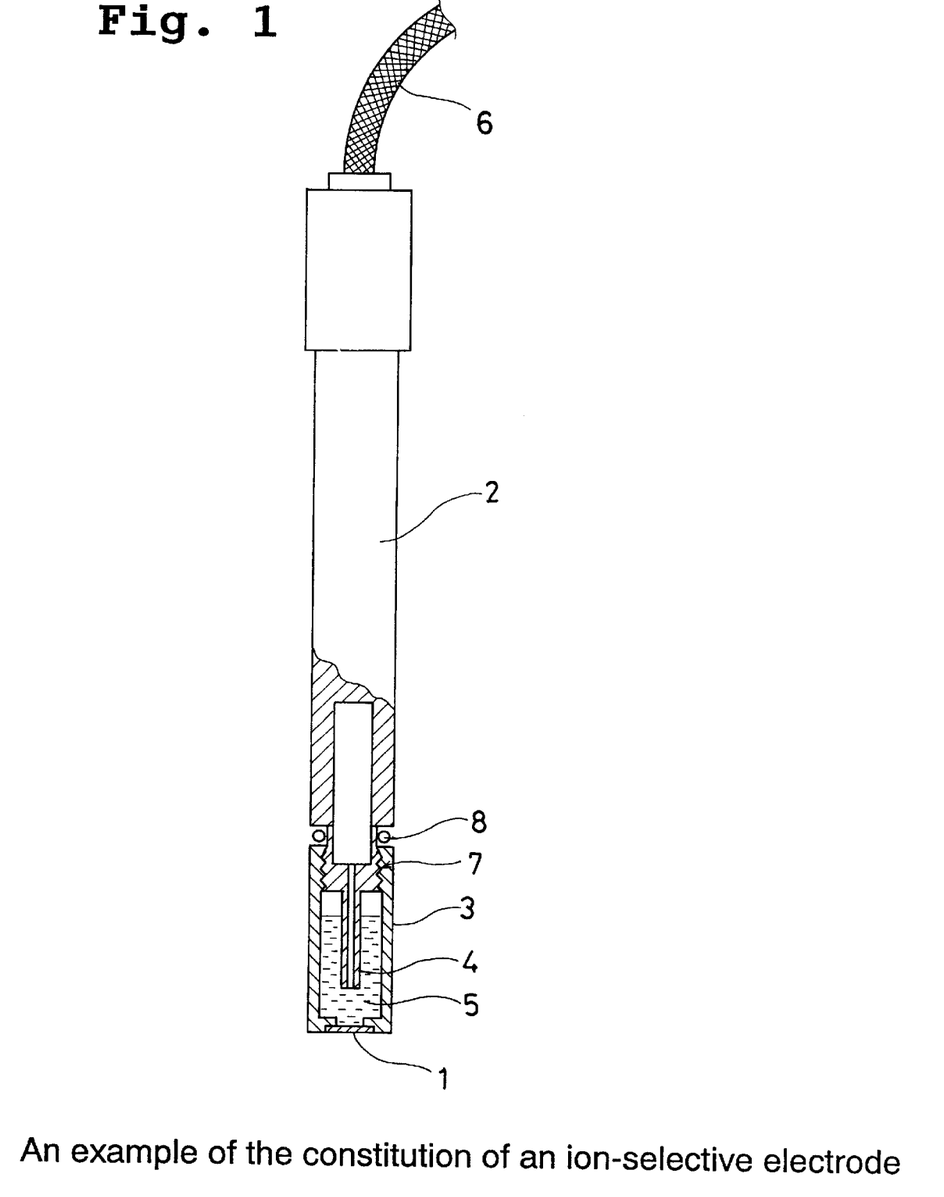
FIG. 1 is a side view showing an example of the structure of the ion-selective electrode by means of a partial cutting.

In FIG. 1, the structure is that an ion-sensing membrane 1 was attached to the chip 3 which was screwed to an end of the electrode body 2 and that an inner solution 5 was filled between the said membrane and the inner electrode 5 extending from the electrode body 2 to the inner part of the chip 3. In FIG. 1, 6 is a shield wire connecting the electrode body 2 to a measuring device (not shown); 7 is a screw part; and 8 is an O-ring. Membrane compositions of the above-mentioned ion-sensing membranes used in this example are shown in Table 1.

Incidentally, the electrodes manufactured using 4% by weight each of peptide [1] Ac-(APPA)$_2$, peptide [2] Ac-(PAPA)$_2$, peptide [3] Ac-(PPAA)$_2$, peptide [4] Ac-(APAP)$_2$, peptide [5] Ac-(PAAP)$_2$ or peptide [6] Ac-(AAPP)$_2$ as an ion-sensing material are named electrode [1], electrode [2], electrode [3], electrode [4], electrode [5] and electrode [6], respectively.

TABLE 1

Membrane Compositions of Ion-selective Electrodes using Peptide

| Electrodes [1]–[6] | [1] | [2] | [3] | [4] | [5] | [6] |
|---|---|---|---|---|---|---|
| Ion-Sensing Material Peptide (4 wt %) | 4.2 mg | 4.3 mg | 5.0 mg | 4.2 mg | 5.7 mg | 4.4 mg |
| Additive Salt TFPB (1 wt %) | 1.1 mg | 1.1 mg | 1.3 mg | 1.1 mg | 1.4 mg | 1.1 mg |
| Plasticizer NPOE, (65 wt %) | 74.7 mg | 69.8 mg | 82.2 mg | 67.9 mg | 91.9 mg | 71.6 mg |
| Membrane Material PVC (30 wt %) | 31.7 mg | 32.3 mg | 37.5 mg | 31.5 mg | 42.8 mg | 33.0 mg |

[1] Ac-(APPA)$_2$, [2] Ac-(PAPA)$_2$, [3] Ac-(PPAA)$_2$, [4] Ac-(APAP)$_2$, [5] Ac-(PAAP)$_2$, [6] Ac-(AAPP)$_2$

After the PVC membrane was completely dried and the chip was dipped in an aqueous solution (about $10^{-2}$M) of calcium nitrate for a whole day and night to carry out a conditioning. After that, the same solution as above when a conditioning was carried out was used as an inner solution and filled in the chip. At that time, the chip was carefully tapped in order to remove the foams existing at the inner side of the PVC membrane so that the inner solution was made completely contacted to the inner side of the membrane. After that, screw of the electrode chip was carefully tightened not to break the membrane and then installed in an electrode kit. In the reference electrode, a 3M saturated potassium chloride solution was used as an inner solution while a $10^{-1}$M lithium acetate solution was used as an outer solution.

(5) Measurement of various ions

Four kinds of standard solutions ($10^{-7}$M~$10^{-1}$M) of Ca(NO$_3$)$_2$, NaNO$_3$, KNO$_3$ and Mg(NO$_3$)$_2$ were successively measured from the low-concentration solution for two rounds using six kinds of ion-selective electrodes. Five kinds of standard solutions ($10^{-7}$M~$10^{-1}$M) of Ni(NO$_3$)$_2$, Cd(NO$_3$)$_2$, Pb(NO$_3$)$_2$, Zn(NO$_3$)$_2$ and Cu(NO$_3$)$_2$ were measured in a similar manner.

(6) Measurement as a lead ion sensor

Inject Method

Since the response of the sensor to lead ion was good in the measurement of various ions, a lead ion-selective electrode was prepared using a $10^{-3}$M aqueous solution of Pb(NO$_3$)$_2$ for a conditioning solution. Aqueous solutions of Pb(NO$_3$)$_2$ from $10^{-6}$M to $10^{-1}$M were successively measured from the low-concentration solution for two rounds using six kinds of electrodes ([1]–[6]) using a $10^{-3}$ aqueous solution of KCl as an inner solution. Changes in concentration of the solution were carried out by means of an inject method where a high-concentration solution was added to a low-concentration solution. Changes in the concentration of the solution to be measured by the inject method are shown in Table 2.

TABLE 2

Concentration Changes of Measured Solution by Inject Method

| Concentration of the Solution to be Measured | Concentration of the Added Solution | Added Amount |
|---|---|---|
| 1 × 10$^{-6}$M | 10$^{-4}$M | 206 μl |
| 3 × 10$^{-6}$M | 10$^{-3}$M | 72 μl |
| 1 × 10$^{-5}$M | 10$^{-3}$M | 212 μl |
| 3 × 10$^{-5}$M | 10$^{-2}$M | 74 μl |
| 1 × 10$^{-4}$M | 10$^{-2}$M | 218 μl |
| 3 × 10$^{-4}$M | 10$^{-1}$M | 76 μl |
| 1 × 10$^{-3}$M | 10$^{-1}$M | 224 μl |
| 3 × 10$^{-3}$M | 1M | 78 μl |
| 1 × 10$^{-2}$M | 1M | 230 μl |
| 3 × 10$^{-2}$M | | |

When the concentration of the solution to be measured was 1×10$^{-1}$M, the measurement was carried out by a means of a direct immersing into the solution of this concentration.

Activity

Then, ten kinds of Pb(NO$_3$)$_2$ mixed solutions ($10^{-6}$M~$10^{-1}$M) each containing an interfering ion ($10^{-1}$M) were successively measured from the low-concentration solution for two rounds using a system of the electrode [3] Ac-(PPAA)$_2$ showing a particularly good sensor response and a lead ion sensor of a system of an electrode [6] Ac-(AAPP)$_2$. However, since the response to aqueous solutions of Pb(NO$_3$)$_2$ coexisting $10^{-1}$M of each Na$^+$ and K$^+$ was difficult in a system of the electrode [3] Ac-(PPAA)$_2$, concentration of the interfering ion was made $10^{-2}$M and the measurement was carried out once again. Table 3 shows activity values of Pb$^{2+}$ ion when each concentration of aqueous solutions of Pb(NO$_3$)$_2$ was converted to activity and the each interfering ion was mixed therewith.

TABLE 3

Activity Values of Pb$^{2+}$ versus Concentrations of Aqueous Solution of Pb(NO$_3$)$_2$

| | Activity Value (log a) | | | |
|---|---|---|---|---|
| Concentration (M) | Pb$^{2+}$ only | Coexisting with 10$^{-M}$ of Na$^+$, K$^+$ or Li$^+$ | Coexisting with 10$^{-1}$M of Ca$^{2+}$, Mg$^{2+}$ Ni$^{2+}$, Cd$^{2+}$ Zn$^{2+}$ or Cu$^{2+}$ | Coexisting with 10$^{-2}$M of Na$^+$ or K$^+$ |
| 1 × 10$^{-6}$ | −6.00 | −6.33 | −6.49 | −6.13 |
| 3 × 10$^{-6}$ | −5.53 | −5.86 | −6.02 | −5.65 |
| 1 × 10$^{-5}$ | −5.01 | −5.33 | −5.49 | −5.13 |
| 3 × 10$^{-5}$ | −4.54 | −4.86 | −5.02 | −4.65 |
| 1 × 10$^{-4}$ | −4.03 | −4.33 | −4.49 | −4.13 |
| 3 × 10$^{-4}$ | −3.57 | −3.86 | −4.02 | −3.66 |
| 1 × 10$^{-3}$ | −3.09 | −3.34 | −3.49 | −3.15 |
| 3 × 10$^{-3}$ | −2.66 | −2.87 | −3.02 | −2.71 |
| 1 × 10$^{-2}$ | −2.24 | −2.37 | −2.50 | −2.26 |
| 3 × 10$^{-2}$ | −1.88 | −1.95 | −2.04 | −1.89 |
| 1 × 10$^{-1}$ | −1.49 | −1.51 | −1.54 | −1.50 |

Results of response of the sensors for various ions using the electrodes [1]–[6] are shown in FIG. 3 to FIG. 10.

Selectivity Coefficients

Figure 2:
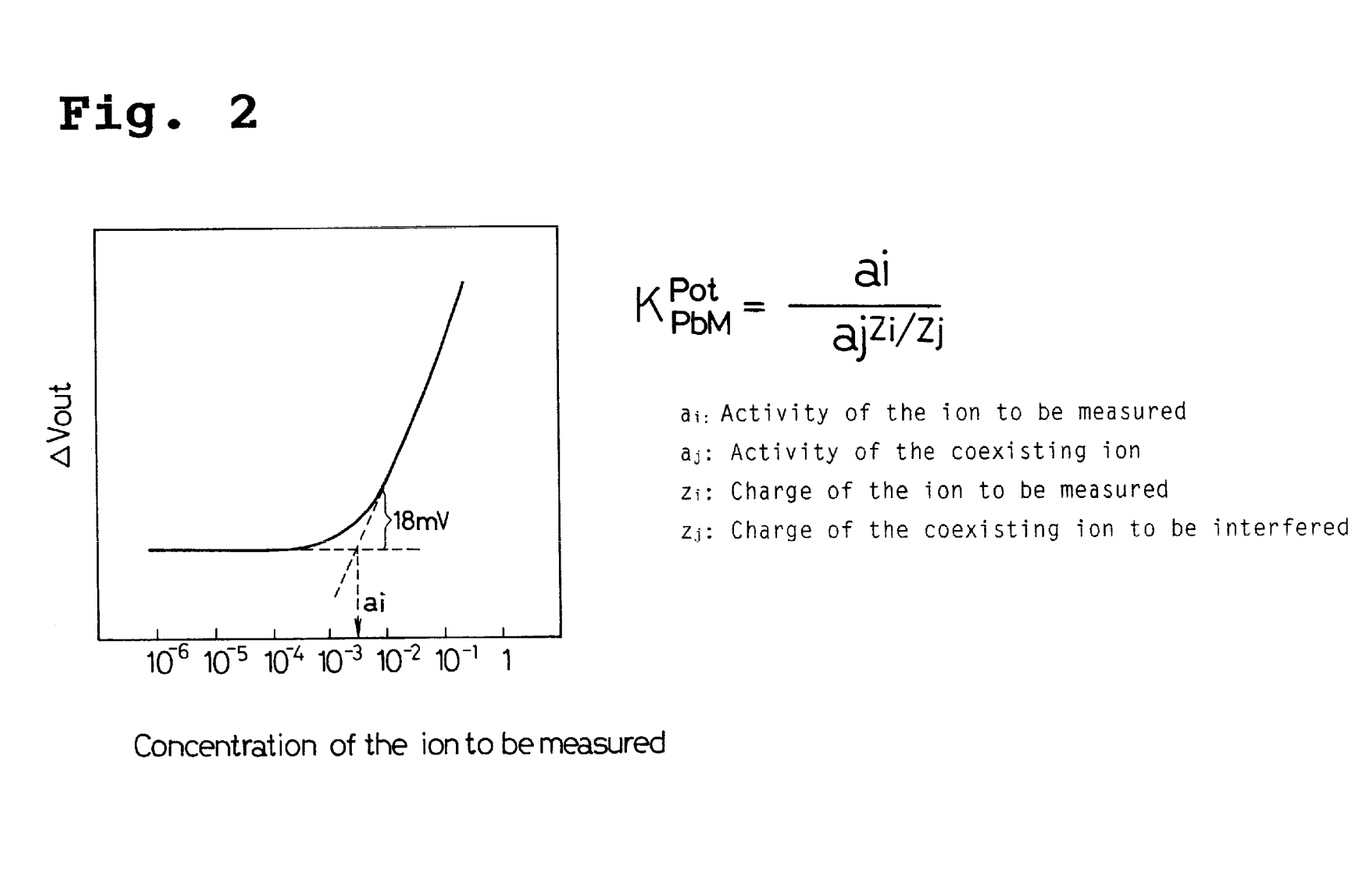
FIG. 2 shows a method for calculating the selective coefficient.
Figure 3:
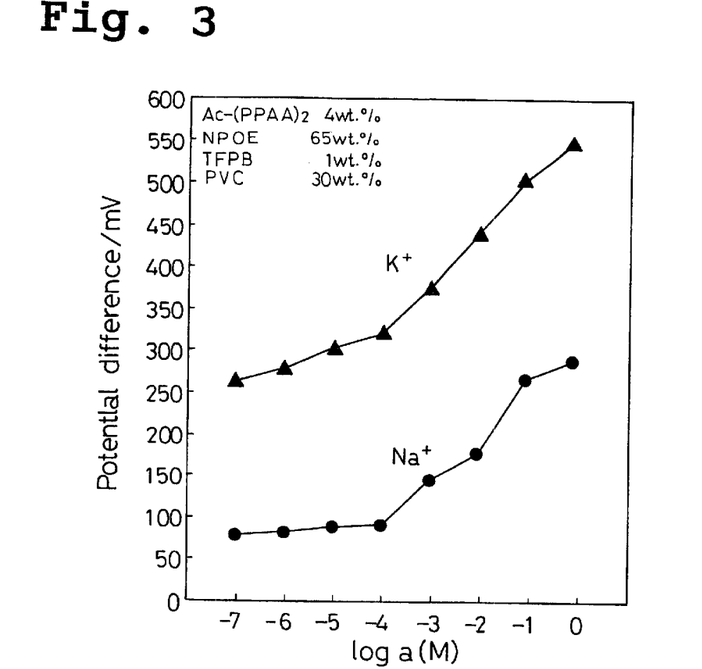
FIG. 3 shows a sensor response of a monovalent ion of the electrode [3] in an Ac-(PPAA)$_2$ system.
Figure 4:
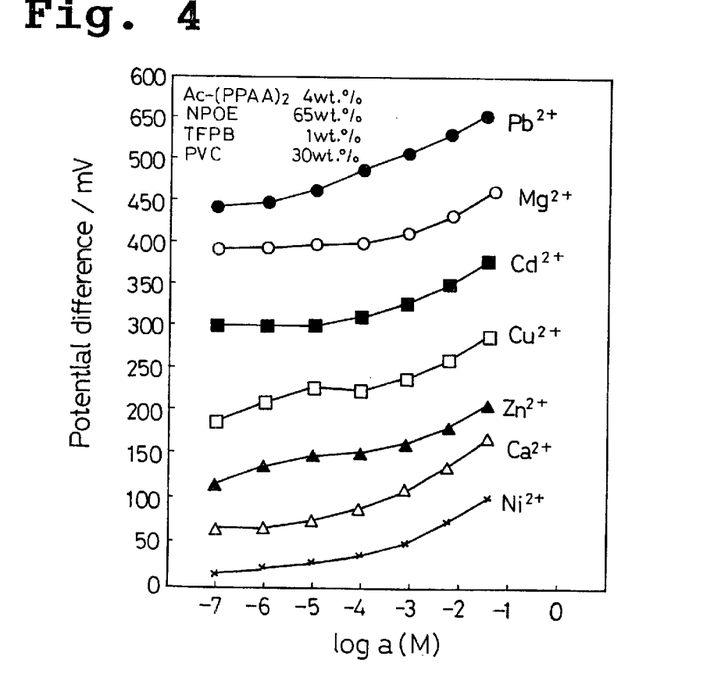
FIG. 4 shows a sensor response of a divalent ion of the electrode [3] in an Ac-(PPAA)$_2$ system.
Figure 5:
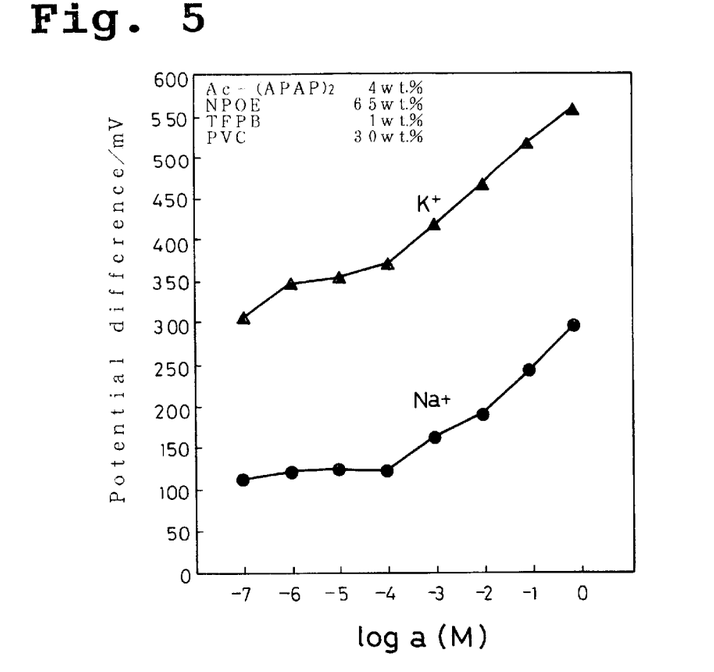
FIG. 5 shows a sensor response of a monovalent ion of the electrode [4] in an Ac-(APAP)$_2$ system.
Figure 6:
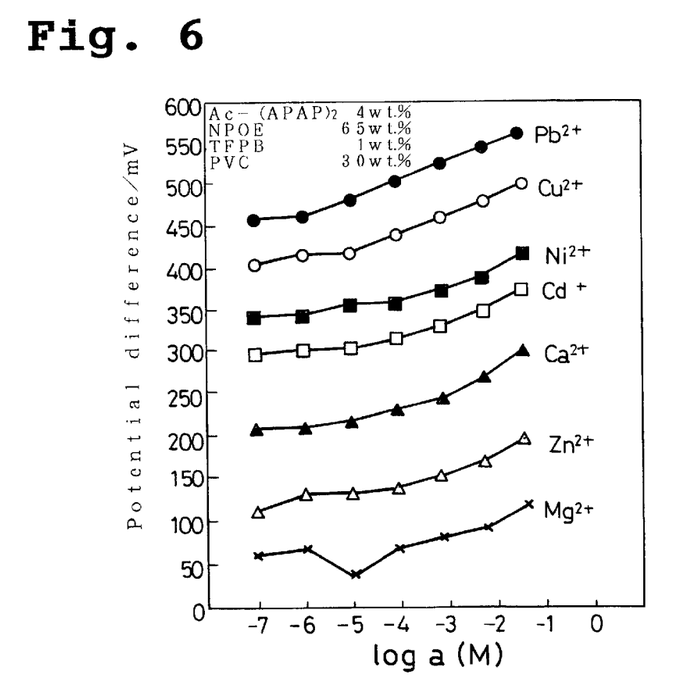
FIG. 6 shows a sensor response of a divalent ion of the electrode [4] in an Ac-(APAP)$_2$ system.
Figure 7:
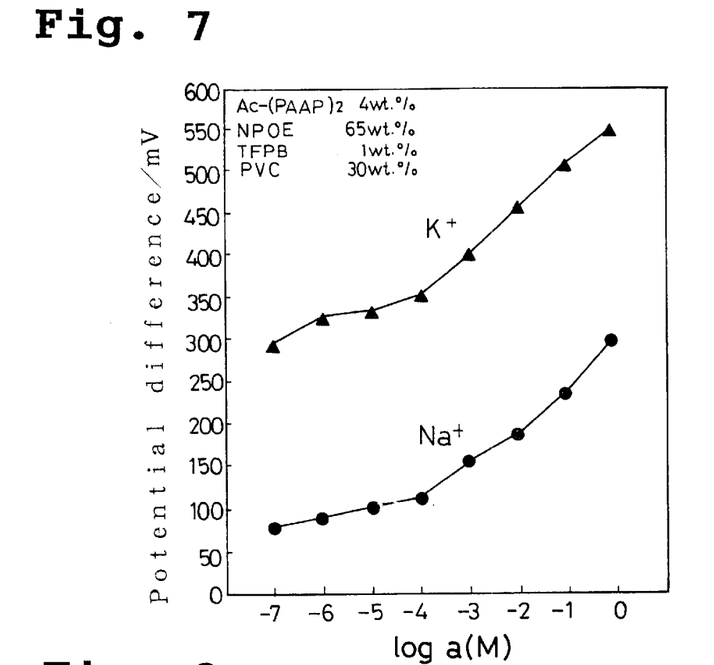
FIG. 7 shows a sensor response of a monovalent ion of the electrode [5] in an Ac-(PAAP)$_2$ system.
Figure 8:
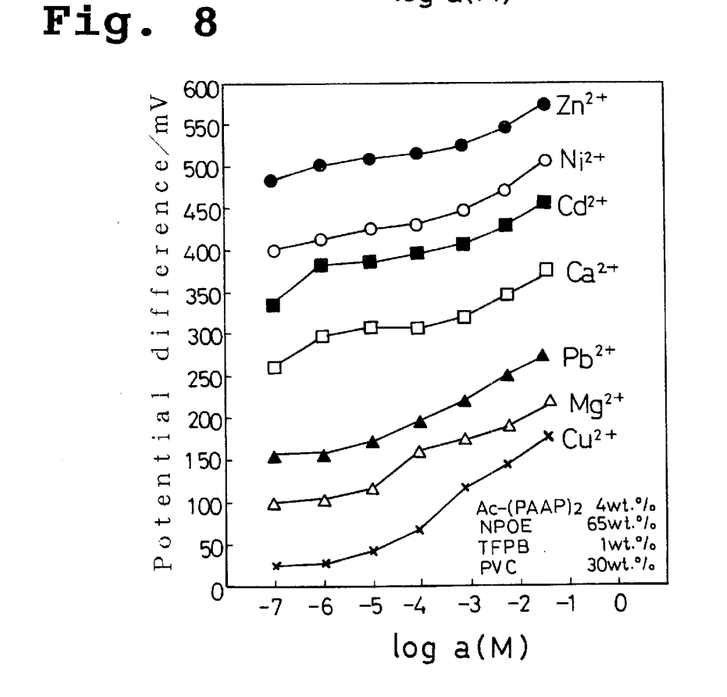
FIG. 8 shows a sensor response of a divalent ion of the electrode [5] in an Ac-(PAAP)$_2$ system.
Figure 9:
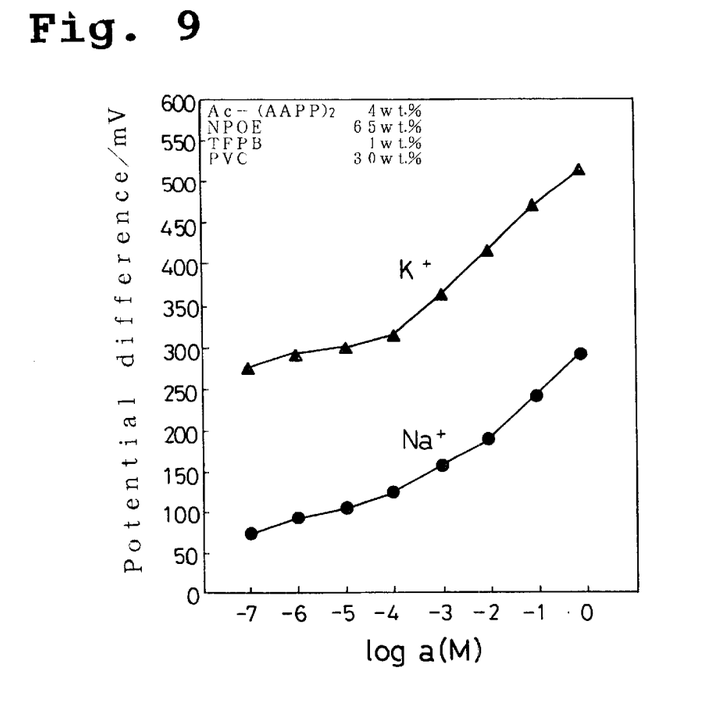
FIG. 9 shows a sensor response of a monovalent ion of the electrode [6] in an Ac-(AAPP)$_2$ system.
Figure 10:
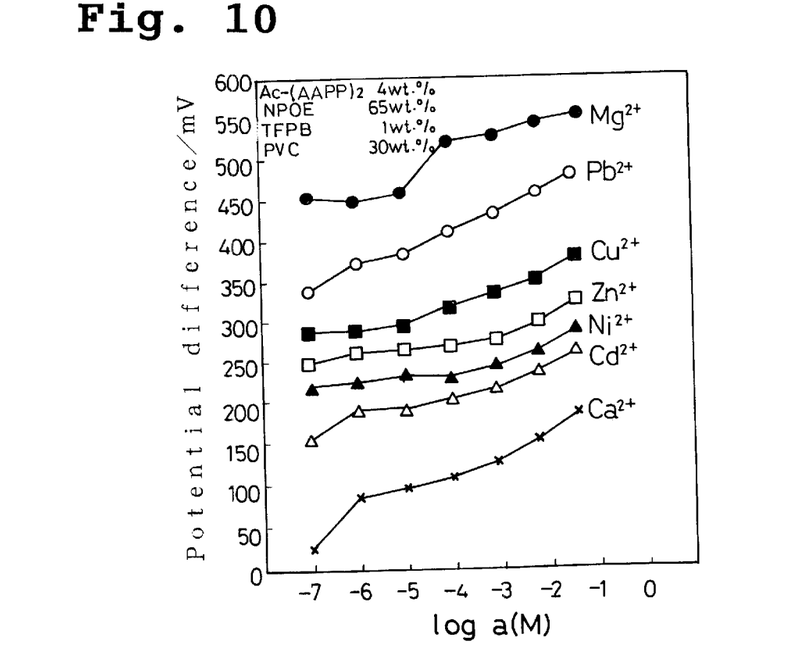
FIG. 10 shows a sensor response of a divalent ion of the electrode [6] in an Ac-(AAPP)$_2$ system.

When an ion sensor analyzes and determines a specific ion only, there is a selectivity coefficient which is an index for its selectivity. In the present invention, the selectivity coefficient was calculated by a mixed solution method. When an ion to be measured (i) is increased in a solution containing a predetermined concentration of an interfering ion (j), there are two areas as shown in FIG. 2, i.e. an area where no potential change takes place by the coexisting ion in the initial stage and another region where potential changes in proportion to the concentration of the ion to be measured. From the crossed point of the tangents of those region is measured the activity ($a_i$) of the ion to be measured and then a selectivity coefficient is calculated from the activity ($a_j$) of the coexisting ion using the formula (6) in FIG. 2.

(7) Response characteristics of lead ion

Figure 11:
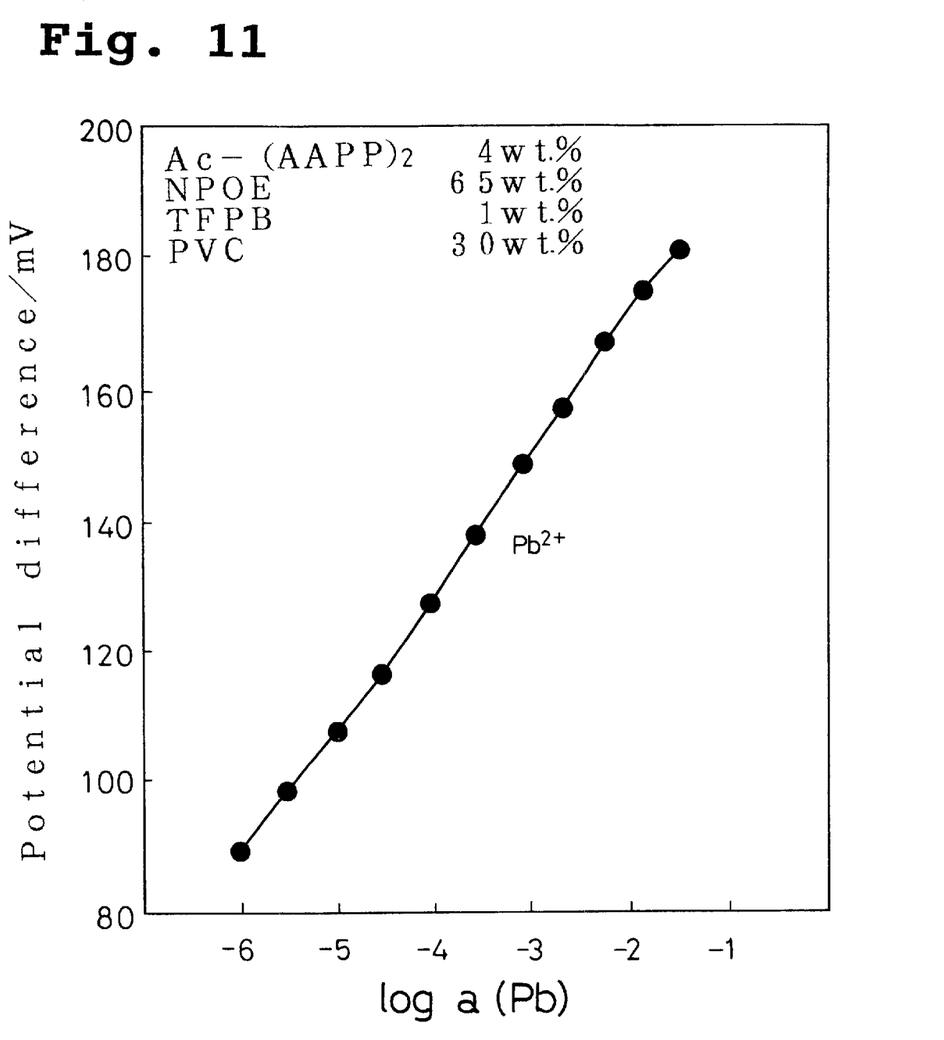
FIG. 11 shows a lead ion sensor response of the electrode [6] in an Ac-(AAPP)$_2$ system.

Potentials of lead ion in the system of the electrode [3] Ac-(PPAA)$_2$ and the electrode [6] Ac-(AAPP)$_2$ where the sensor response to lead ion was particularly good were measured again. Result of sensor response to lead ion is shown in FIG. 11. In the systems of the electrode [3] and the electrode [6], a linear response was achieved within a wide range of $10^{-6}$M~$10^{-1}$M.

It has now been made clear that a noncyclic peptide having a structure in which two amino acid units are repeated is excellent as an ion-selective electrode to lead ion, etc.

(8) Selectivity of lead ion sensor

Figure 12:
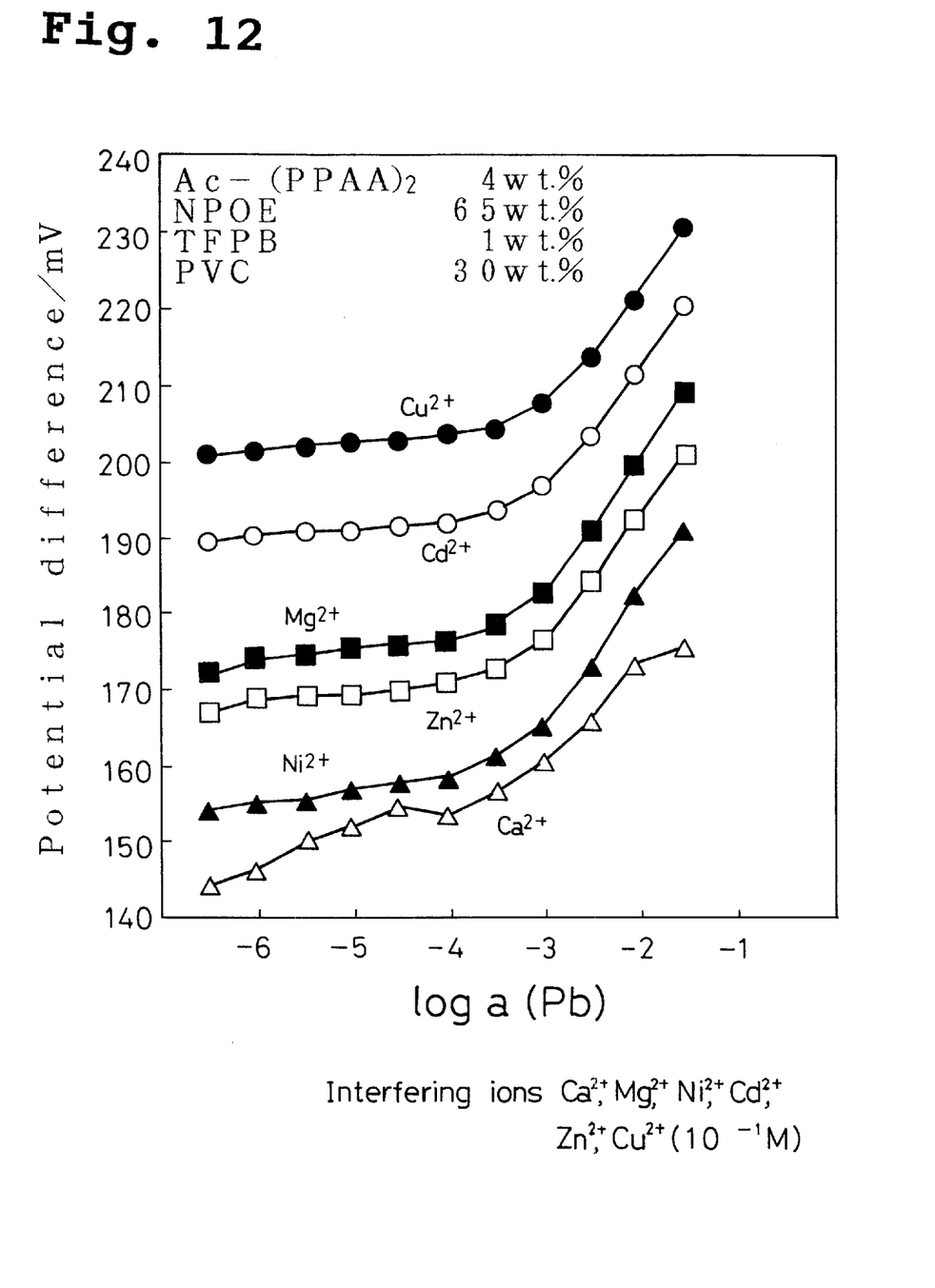
FIG. 12 shows a sensor response in a Pb(NO$_3$)$_2$ mixed solution where a divalent interfering ion is made coexisted in a lead ion sensor of an Ac-(PPAA)$_2$ system of the electrode [3].
Figure 13:
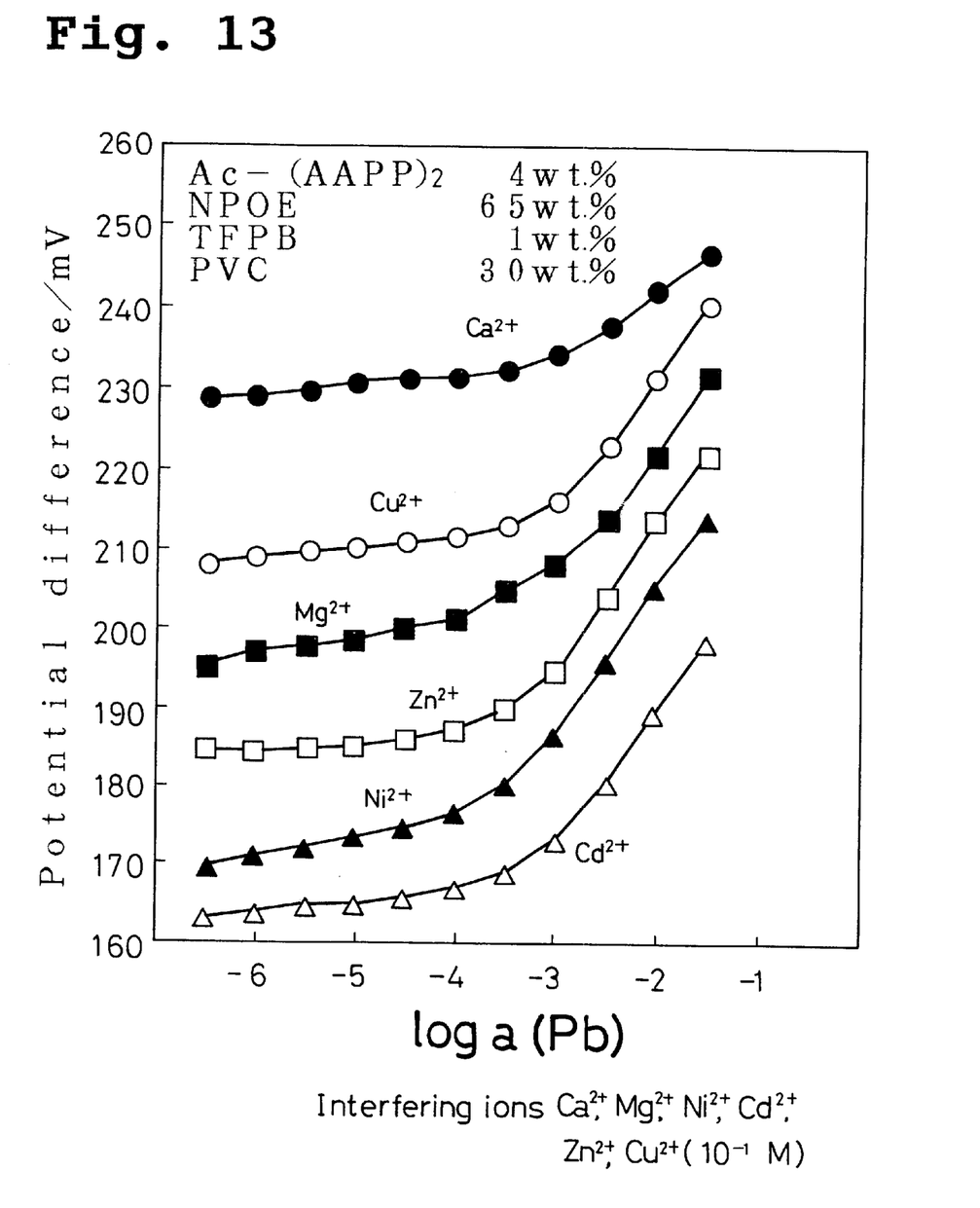
FIG. 13 shows a sensor response in a Pb(NO$_3$)$_2$ mixed solution where a divalent interfering ion is made coexisted in a lead ion sensor of an Ac-(AAPP)$_2$ system of the electrode [6].
Figure 14:
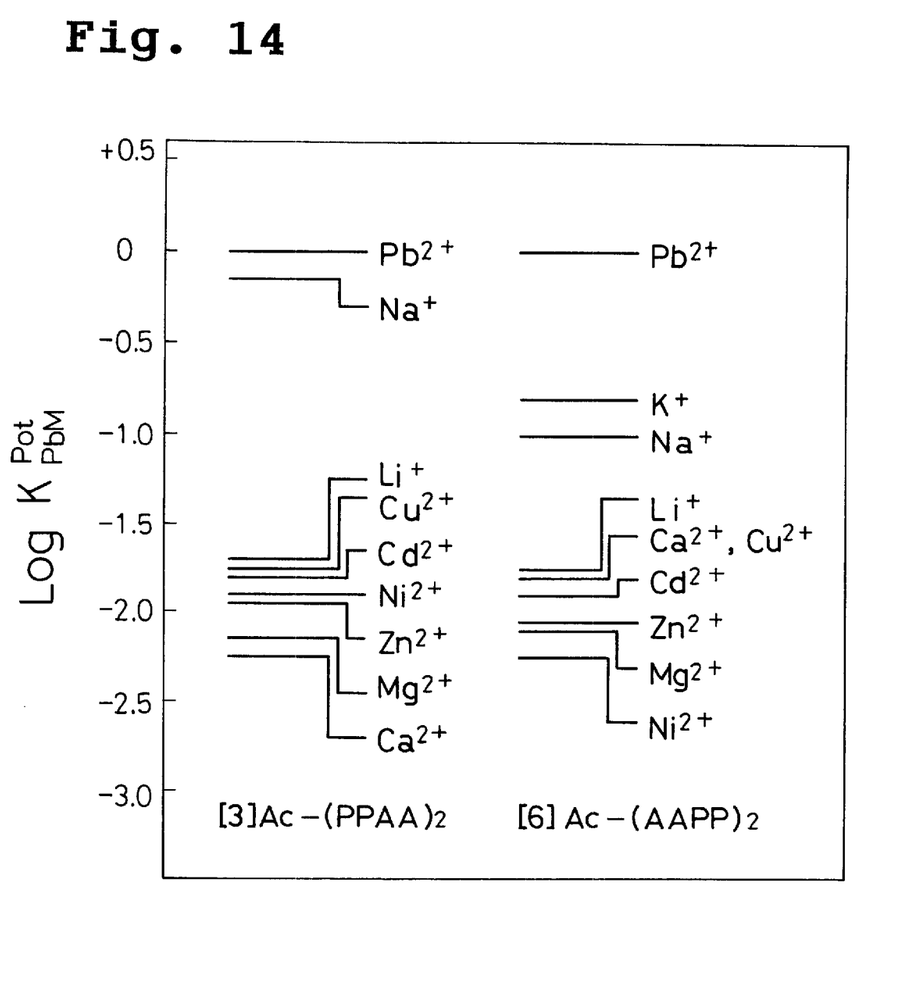
FIG. 14 is a graph showing a comparison of values of selectivity coefficients.

FIGS. 12 and 13 show the result of sensor responses in a Pb(NO$_3$)$_2$ mixed solutions where ten kinds of interfering ions each coexisted using a system of the electrode [3] Ac-(PPAA)$_2$ and a system of the electrode [6] Ac-(AAPP)$_2$. In addition, results to each interfering ion are summarized in FIG. 14.

(9) Response velocity of lead ion sensor

Figure 15:
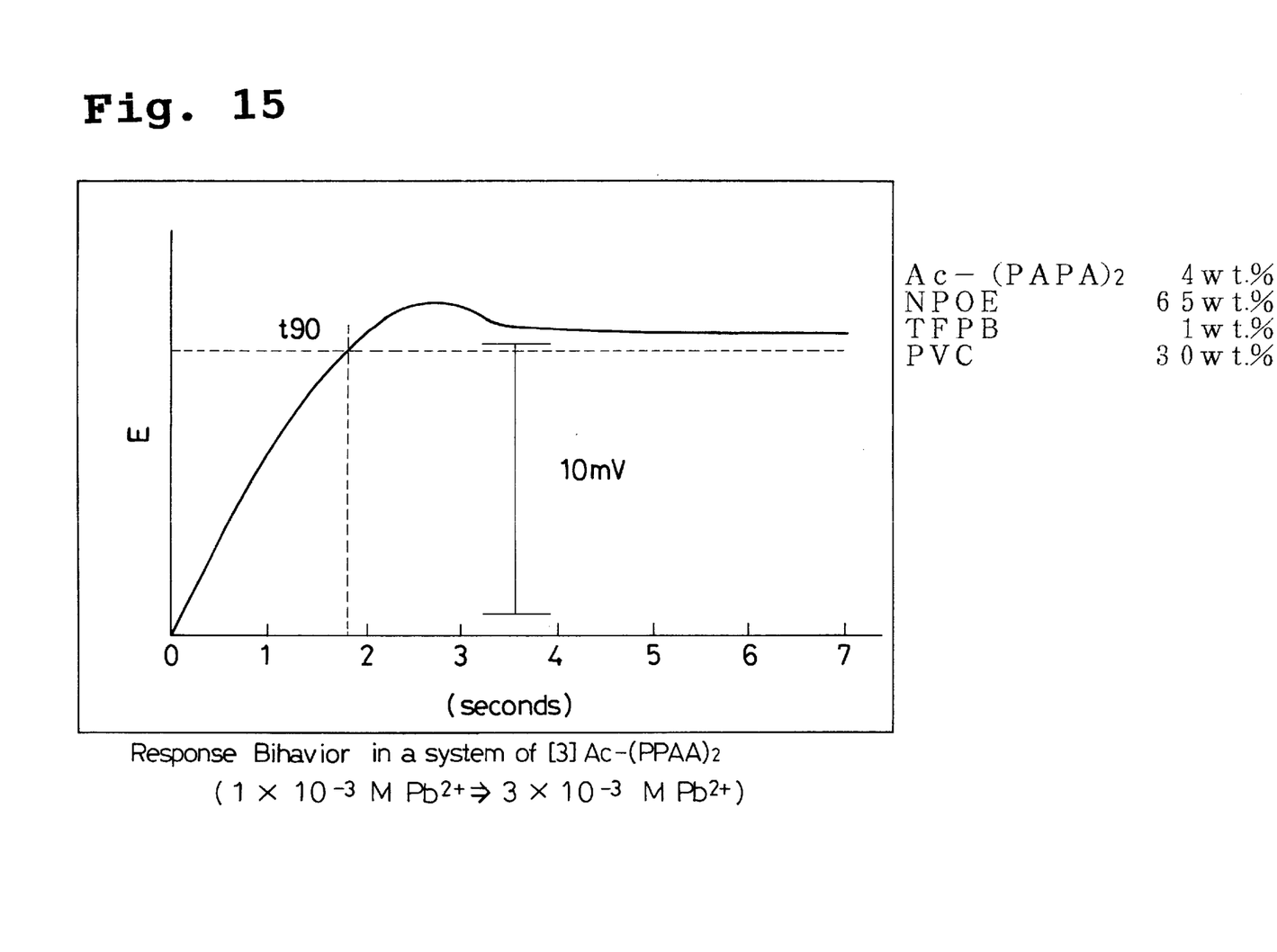
FIG. 15 shows a response behavior of the Ac-(PPAA)$_2$ system of the electrode [3] to lead ion.
Figure 16:
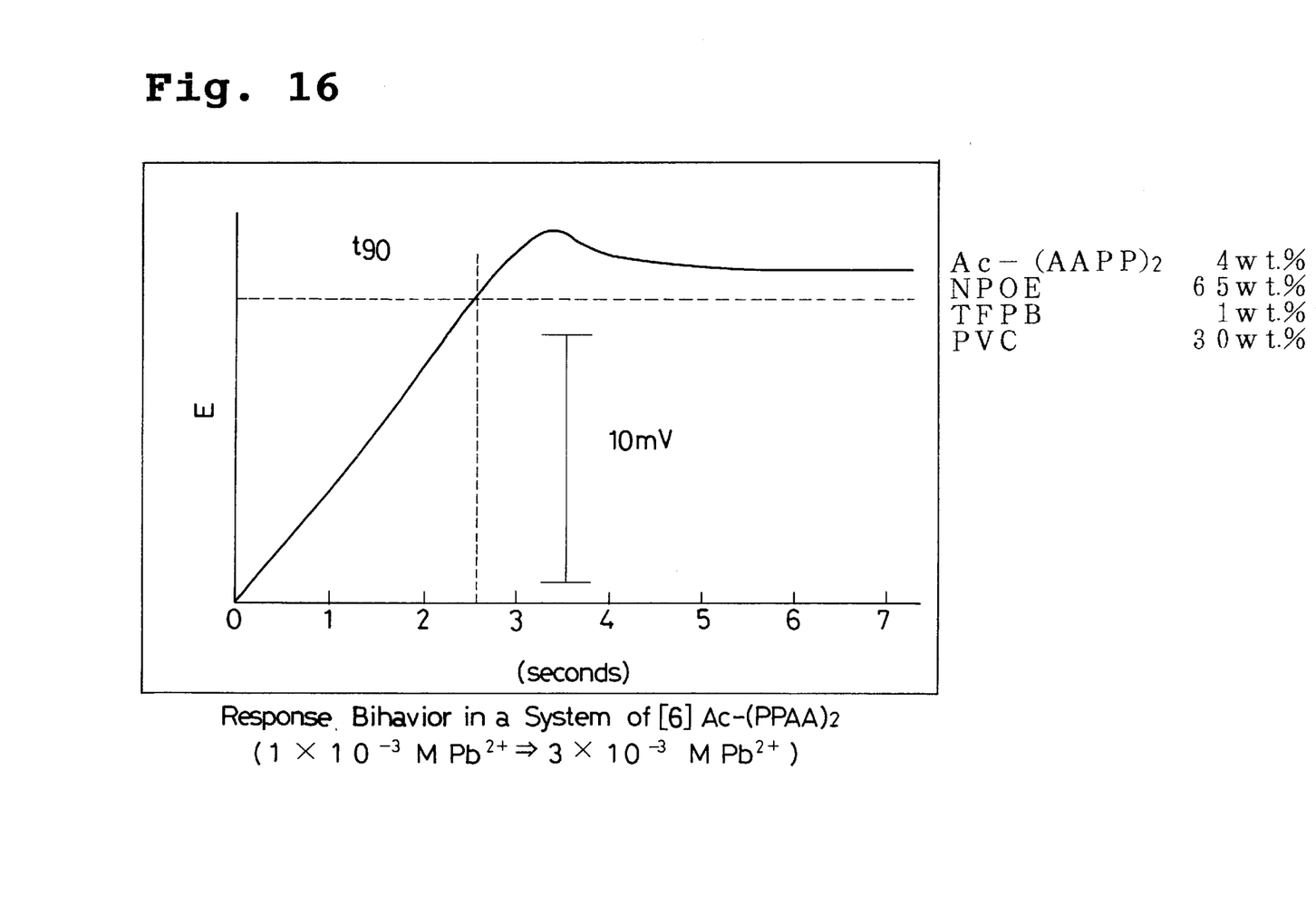
FIG. 16 shows a response behavior of the Ac-(AAPP)$_2$ system of the electrode [6] to lead ion.

In a practical use of the ion sensor, it is an important thing that how quick the sensor response is when the concentration of the ion to be measured is changed. FIGS. 15 and 16 show the changes in potential when the ion concentration is changed from $1 \times 10^{-3}$M to $3 \times 10^{-3}$ M. When the time ($t_{90}$) until a 90% response of the lead ion sensor was measured, the response time was about 2 seconds in the system of the electrode [3] Ac-(PPAA)$_2$ and was about 3 seconds in the system of the electrode [6] Ac-(AAPP)$_2$.

Examples of response characteristics of the electrodes using the noncyclic peptides are shown in Table 4.

TABLE 4

Response characteristics of sensors using noncyclic peptides

| Noncyclic Peptides | Response characteristics |
| --- | --- |
| Ac- (APPA)$_2$ | $Mg^{2+}$ |
| Ac- (PAPA)$_2$ | $Pb^{2+}$ |
| Ac- (PPAA)$_2$ | $Pb^{2+}$, $K^+$, $Ca^{2+}$, $Ni^{2+}$ |
| Ac- (APAP)$_2$ | $Pb^{2+}$, $Cu^{2+}$, $Ca^{2+}$ |
| Ac- (PAAP)$_2$ | $Pb^{2+}$, $Cu^{2+}$, $Zn^{2+}$, $Ni^{2+}$ |
| Ac- (AAPP)$_2$ | $Pb^{2+}$, $Cu^{2+}$, $Ca^{2+}$, $Cd^{2+}$ |

What is claimed is:

1. An ion sensor comprising an ion-selective electrode having a sensing membrane containing a non-cyclic peptide comprising at least two of natural amino acids or non-natural amino acids in a total number of 4–20; wherein the non-cyclic peptide is not poly-glutamic acid chains.

2. An ion sensor as claimed in claim 1, wherein the total number of amino acids is 5–12.

3. As ion sensor as claimed in claim 2, in which the amino acids are selected from the class consisting of alanine, proline, valine, leucine, serine, tryptophan, asparagine and histidine.

4. An ion sensor as claimed in claim 3, wherein the noncyclic peptide has at least two amino acid sequences each in two recurrences.

5. An ion sensor as claimed in claim 4, wherein the ion sensing membrane is used for the ion-selective electrode of an ion-selective field effect transistor.

6. An ion sensor as claimed in claim 3, wherein the ion sensing membrane is used for the ion-selective electrode of an ion-selective field effect transistor.

7. An ion sensor as claimed in claim 2, wherein the noncyclic peptide has at least two amino acid sequences each in two recurrences.

8. An ion sensor as claimed in claim 7, wherein the ion sensing membrane is used for the ion-selective electrode of an ion-selective field effect transistor.

9. An ion sensor as claimed in claim 2, wherein the ion sensing membrane is used for the ion-selective electrode of an ion-selective field effect transistor.

10. As ion sensor as claimed in claim 1, in which the amino acids are selected from the class consisting of alanine, proline, valine, leucine, serine, tryptophan, asparagine and histidine.

11. An ion sensor as claimed in claim 10, wherein the noncyclic peptide has at least two amino acid sequences each in two recurrences.

12. An ion sensor as claimed in claim 11, wherein the ion sensing membrane is used for the ion-selective electrode of an ion-selective field effect transistor.

13. An ion sensor as claimed in claim 10, wherein the ion sensing membrane is used for the ion-selective electrode of an ion-selective field effect transistor.

14. An ion sensor as claimed in claims 1, wherein the noncyclic peptide has at least two amino acid sequences each in two recurrences.

15. An ion sensor as claimed in claim 14, wherein the ion sensing membrane is used for the ion-selective electrode of an ion-selective field effect transistor.

16. An ion sensor as claimed in claim 1, wherein the ion sensing membrane is used for the ion-selective electrode of an ion-selective field effect transistor.

* * * * *